US012697241B1

(12) United States Patent
Walloch

(10) Patent No.: US 12,697,241 B1
(45) Date of Patent: Aug. 4, 2026

(54) BACK BRACE FOR SITTING

(71) Applicant: MAGICALLY PAIN FREE, LLC, Vancouver, WA (US)

(72) Inventor: Cara Walloch, Vancouver, WA (US)

(73) Assignee: Magically Pain Free, LLC

( * ) Notice: Subject to any disclaimer, the term of this patent is extended or adjusted under 35 U.S.C. 154(b) by 1477 days.

(21) Appl. No.: 17/153,829

(22) Filed: Jan. 20, 2021

Related U.S. Application Data

(60) Provisional application No. 62/964,002, filed on Jan. 21, 2020.

(51) Int. Cl.
    *A61F 5/02*          (2006.01)
    *A47C 7/02*          (2006.01)
    *A47C 7/42*          (2006.01)

(52) U.S. Cl.
    CPC .............. *A61F 5/026* (2013.01); *A47C 7/021* (2013.01); *A47C 7/42* (2013.01)

(58) Field of Classification Search
    CPC .. A61F 5/00; A61F 5/01; A61F 5/0102; A61F 5/0125; A61F 5/02; A61F 5/024; A61F 5/026; A61F 5/028; A61F 5/042; A61F 5/0585; A61F 2005/0181; A61F 2005/0197; A61F 2005/0132; A47C 7/02; A47C 7/021; A47C 7/0213; A47C 7/16; A47C 7/18; A47C 7/28; A47C 7/34; A47C 7/40; A47C 7/407; A47C 7/42; A47C 7/425; A47C 7/46; A47C 7/462; A47C 13/00; A61G 5/14; A41D 13/0531; A47D 1/02; A47D 1/10

USPC .............. 224/625, 627, 637, 638, 647, 648; 602/16; 601/23, 24, 49, 58
    See application file for complete search history.

(56) References Cited

U.S. PATENT DOCUMENTS

| | | | | |
|---|---|---|---|---|
| 5,108,202 A | * | 4/1992 | Smith | A61G 5/128 |
| | | | | 297/DIG. 10 |
| 5,452,868 A | * | 9/1995 | Kanigowski | B60N 2/6671 |
| | | | | 297/284.4 |
| 5,803,545 A | * | 9/1998 | Guguin | A61G 5/14 |
| | | | | 297/DIG. 10 |
| 6,007,156 A | * | 12/1999 | Chang | B60N 2/265 |
| | | | | 297/485 |
| 8,702,177 B1 | * | 4/2014 | Hogue | A61F 5/3769 |
| | | | | 297/484 |
| 2011/0298260 A1 | * | 12/2011 | Hsuan-Chin | A47C 7/402 |
| | | | | 297/284.7 |

(Continued)

*Primary Examiner* — Alireza Nia
*Assistant Examiner* — Gina Mccarthy
(74) *Attorney, Agent, or Firm* — Kenneth C. Booth; Booth Udall, PLC

(57) ABSTRACT

A back brace for sitting is disclosed, having a frame with a back portion hingedly coupled to a seat portion, and a support mechanism coupled to the back portion and able to expand and contract the back portion, changing the distance between the top end of the back portion and the hinge. The brace also includes shoulder straps coupled to the back portion of the frame, looping under a user's arms, as well as an abdominal strap coupled to the back portion and configured to encircle the user. The brace also comprises a seat cushion coupled to the seat portion of the frame. The support mechanism reduces the force exerted on the user's back by supporting the user with the back portion of the frame and driving an upper portion of the user's back away from a lower portion of the user's back.

20 Claims, 6 Drawing Sheets

(56) References Cited

U.S. PATENT DOCUMENTS

| | | | |
|---|---|---|---|
| 2018/0050449 A1* | 2/2018 | Stefan | .................... B25J 9/0006 |
| 2018/0279804 A1* | 10/2018 | Romero | .............. A47D 15/006 |

* cited by examiner

100

112

110

114

102

116

106

120

104

108

124

122

124

118

BACK BRACE FOR SITTING

RELATED APPLICATIONS

This application claims the benefit of U.S. provisional patent application 62/964,002, filed Jan. 21, 2020 titled "Back Brace for Sitting," the entirety of the disclosure of which is hereby incorporated by this reference.

TECHNICAL FIELD

Aspects of this document relate generally to a back brace for sitting.

BACKGROUND

Braces can be an important part of treatment and recovery for back injuries. They help an individual maintain a posture conducive to healing, and can also alleviate pain by reducing the strain or pressure being exerted on the user. Braces can make up a large part of a person's treatment program that takes place away from their practitioner; its effectiveness can be severely limited when a user does not use the brace as instructed. Discomfort and difficult instructions quickly motivate a user to deviate from the prescribed use of the brace. Conventional braces have attempted to improve compliance by simplifying the braces and making them more comfortable, but these efforts are often at the cost of efficacy. For example, inflatable braces may be more comfortable and easier to use than other conventional braces, but they do not exert sufficient force to alleviate pressure (and pain) in the middle back, or the retraction of over flexed shoulders. Furthermore, conventional braces are often outside the price range of the typical user. For example, a typical budget may be in the neighborhood of $150, while conventional braces range from $300 to $2000, or more.

SUMMARY

According to one aspect, a back brace for sitting includes a frame having a back portion hingedly coupled to a seat portion at a hinge point through a biased hinge. The back portion is flexible and has a top end and a bottom end distal to the top end and proximate the hinge point. The back brace also includes a support mechanism pivotably coupled to the back portion of the frame. The support mechanism is a gas spring able to expand and contract the back portion of the frame, changing the distance between the top end of the back portion of the frame and the hinge point. The back brace further includes a first pair of shoulder straps coupled to the back portion of the frame, looping under a user's arms, and an abdominal strap releasably coupled to the back portion of the frame and positioned on the back portion between the T8 and L2 vertebrae of the user. The abdominal strap is configured to releasably couple to one of itself and the frame to encircle the user. The brace includes a second pair of shoulder straps, each shoulder strap of the second pair of shoulder straps coupled to the back portion and the abdominal strap, and a seat cushion coupled to the seat portion of the frame. The frame is movable between a standing configuration and a sitting configuration as the user transitions from standing to sitting on the seat cushion. The standing configuration includes a first angle between the seat portion and the back portion. The sitting configuration includes a second angle between the seat portion and the back portion, the second angle smaller than the first angle. The support mechanism reduces the force exerted on the user's back by supporting the user with the back portion of the frame and driving an upper portion of the user's back away from a lower portion of the user's back. The biased hinge is biased to drive the frame toward the sitting configuration.

Particular embodiments may comprise one or more of the following features. The support mechanism may be biased to exert an expanding force on the back portion of the frame, driving the top end of the back portion away from the hinge point. The expanding force may be adjustable by the user. The support mechanism may be movable by the user between an unlocked state where the support mechanism allows the back portion of the frame to expand and contract, and a locked state where the support mechanism prevents the back portion from contracting. The support mechanism may be movable by the user between an unlocked state where the support mechanism allows the back portion of the frame to expand and contract, and a locked state where the support mechanism prevents the back portion from expanding and contracting.

According to another aspect of the disclosure, a back brace for sitting includes a frame having a back portion hingedly coupled to a seat portion at a hinge point through a biased hinge. The back portion is flexible and has a top end and a bottom end distal to the top end and proximate the hinge point. The brace also includes a support mechanism pivotably coupled to the back portion of the frame, the support mechanism able to expand and contract the back portion of the frame, changing the distance between the top end of the back portion of the frame and the hinge point. The brace further includes a first pair of shoulder straps coupled to the back portion of the frame, above the support mechanism, looping under a user's arms, and an abdominal strap releasably coupled to the back portion of the frame and positioned on the back portion between the T8 and L2 vertebrae of the user. The abdominal strap is configured to releasably couple to one of itself and the frame to encircle the user. The brace includes a seat cushion coupled to the seat portion of the frame. The frame is movable between a standing configuration and a sitting configuration as the user transitions from standing to sitting on the seat cushion. The standing configuration includes a first angle between the seat portion and the back portion. The sitting configuration includes a second angle between the seat portion and the back portion, the second angle smaller than the first angle. The support mechanism reduces the force exerted on the user's back by supporting the user with the back portion of the frame and driving an upper portion of the user's back away from a lower portion of the user's back. The biased hinge is biased to drive the frame toward the sitting configuration. The support mechanism is movable by the user between an unlocked state where the support mechanism allows the back portion of the frame to expand and contract, and a locked state where the support mechanism prevents the back portion from contracting.

Particular embodiments may comprise one or more of the following features. The support mechanism may be biased to exert an expanding force on the back portion of the frame, driving the top end of the back portion away from the hinge point. The expanding force may be adjustable by the user. The locked state of the support mechanism may also prevent the back portion from expanding. The support mechanism may be a gas spring. The support mechanism may be a lifting jack.

According to yet another aspect of the disclosure, a back brace for sitting includes a frame having a back portion hingedly coupled to a seat portion at a hinge point. The back portion includes a top end and a bottom end distal to the top end and proximate the hinge point. The brace also includes a support mechanism coupled to the back portion of the frame, the support mechanism able to expand and contract the back portion of the frame, changing the distance between the top end of the back portion of the frame and the hinge point. The brace further includes a first pair of shoulder straps coupled to the back portion of the frame, looping under a user's arms, and an abdominal strap coupled to the back portion of the frame. The abdominal strap is configured to releasably couple to one of itself and the frame to encircle the user. The brace includes a seat cushion coupled to the seat portion of the frame. The frame is movable between a standing configuration and a sitting configuration as the user transitions from standing to sitting on the seat cushion. The standing configuration includes a first angle between the seat portion and the back portion. The sitting configuration includes a second angle between the seat portion and the back portion, the second angle smaller than the first angle. The support mechanism reduces the force exerted on the user's back by supporting the user with the back portion of the frame and driving an upper portion of the user's back away from a lower portion of the user's back.

Particular embodiments may comprise one or more of the following features. The back portion of the frame may be hingedly coupled to the seat portion of the frame through a biased hinge that is biased to drive the frame toward the sitting configuration. The back brace may further include a second pair of shoulder straps, each shoulder strap of the second pair of shoulder straps coupled to the back portion and the abdominal strap. The abdominal strap may be positioned on the back portion of the frame between the T8 and L2 vertebrae of the user. The support mechanism may be pivotably coupled to the back portion of the frame. At least one of the first pair of shoulder straps and the abdominal strap may be releasably coupled to the back portion of the frame.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112 (f). Thus, the use of the words "function," "means" or "step" in the Detailed Description or Description of the Drawings or claims is not intended to somehow indicate a desire to invoke the special provisions of 35 U.S.C. § 112 (f), to define the invention. To the contrary, if the provisions of 35 U.S.C. § 112 (f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112 (f). Moreover, even if the provisions of 35 U.S.C. § 112 (f) are invoked to define the claimed aspects, it is intended that these aspects not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The disclosure will hereinafter be described in conjunction with the appended drawings, where like designations denote like elements, and.

DETAILED DESCRIPTION

Figure 1:
FIG. 1 is a perspective view of a back brace for sitting.

This disclosure, its aspects and implementations, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

While this disclosure includes a number of embodiments in many different forms, there is shown in the drawings and will herein be described in detail particular embodiments with the understanding that the present disclosure is to be considered as an exemplification of the principles of the disclosed methods and systems, and is not intended to limit the broad aspect of the disclosed concepts to the embodiments illustrated.

Braces can be an important part of treatment and recovery for back injuries. They help an individual maintain a posture conducive to healing, and can also alleviate pain by reducing the strain or pressure being exerted on the user. Braces can make up a large part of a person's treatment program that takes place away from their practitioner; its effectiveness can be severely limited when a user does not use the brace as instructed. Discomfort and difficult instructions quickly motivate a user to deviate from the prescribed use of the brace. Conventional braces have attempted to improve compliance by simplifying the braces and making them more comfortable, but these efforts are often at the cost of efficacy. For example, inflatable braces may be more comfortable and easier to use than other conventional braces, but they do not exert sufficient force to alleviate pressure (and pain) in the middle back, or the retraction of over flexed shoulders. Furthermore, conventional braces are often outside the price range of the typical user. For example, a typical budget may be in the neighborhood of $150, while conventional braces range from $300 to $2000, or more.

Contemplated herein is a back brace for sitting that facilitates compliance with a treatment plan through improvements in comfort, efficacy, ease of use, and cost. The brace contemplated herein comprises a frame that is able to expand to relieve pressure on the middle back when the user is sitting, lifting the upper body through shoulder straps and an abdominal strap. The brace is intended for use while sitting, particularly when driving, gaming, or working at a computer. Advantageous over conventional back braces, the brace contemplated herein is not entirely rigid. As will be discussed further, below, the brace has a degree of flexibility that allows a user to shift their position enough to safely drive a car. This flexibility comes from the structure and materials of the brace, which also make the brace less expensive than conventional braces, while still being durable enough to survive an entire treatment regimen. The brace is lightweight and easy to move from one seating location to another. The ease of use, comfort, and low cost all lead to greater patient compliance with a treatment regimen, and thus better results overall.

FIG. 1 is a perspective view of a non-limiting example of a back brace for sitting (hereinafter brace 100). As shown, the brace 100 comprises a frame 102 having an upright back portion 104 and a seat portion 106 that is hingedly coupled to the back portion 104 at a hinge point 118. The frame 102 provides structure to the brace 100, enabling the brace 100 to exert force on the wearer's back to provide relief. The back portion 104 of the frame 102 has a top end 120 and a bottom end 122 opposite the top end 120. The bottom end 122 is at, or near, the point where the back portion 104 and the seat portion 106 are hingedly coupled (i.e. the hinge point 118), which will be discussed in greater detail, below.

As shown, the brace 100 comprises a seat cushion 116 that is coupled to the seat portion 106 of the frame 102. In some embodiments, the seat cushion 116 may be releasably coupled, allowing it to be washed or replaced. For example, in some embodiments, the seat cushion 116 may be coupled to the frame through hook-and-loop fasteners, snaps, magnets, clips, or other releasable surface coupling known in the art. In other embodiments, the seat cushion 116 may be fixedly coupled to the seat portion 106 of the frame 102, or even integral with it.

According to various embodiments, at least some of the frame 102 is composed of a flexible material, enabling it to conform to different seating environments and/or body shapes, while still able to provide sufficient support to the wearer. Specifically, at least some of at least one of the portions of the frame 102 is flexible, meaning it is able to elastically flex or deform while still being rigid enough to maintain a desired shape. In some embodiments, the flexible portion may be composed of any elastically deformable material known in the art including, but not limited to, metal, plastic, thermoplastic, and the like.

In some embodiments, the frame 102 may be composed of a rigid framework coupled with a flexible framework. The flexible portion of the frame 102, or flexible framework, may also serve as a coating element that encloses, or partially encloses, the rigid framework. In other embodiments, the flexible portion of the frame 102 may be separate from the rigid portion, and the portions may be fixedly coupled using methods known in the art to be compatible with the portion materials.

In some embodiments, the frame 102 may comprise one or more tangs 124, which may be coupled to or embedded within a portion of the frame 102. In some embodiments, the tangs 124 may be flat, while in other embodiments, the tangs 124 may be non-planar. In still other embodiments, the tangs 124 may be composed of a material that is both rigid and non-metallic, such as a thermoplastic, or any other material known in the art. As shown in FIG. 1, in some embodiments, the back portion 104 and seat portion 106 of the frame 102 may each comprise a tang 124, and those tangs 124 are hingedly coupled to each other at the hinge point 118. Other embodiments may not employ tangs at all 124.

In other embodiments, one or both portions of the frame 102 may be composed of an integral piece of material with variable thickness and/or density, making some parts rigid and others flexible, providing the needed structure while simplifying manufacture and lowering cost. As a specific example, in one embodiment the frame 102 may be composed of a thermoplastic.

In use, the two frame portions form an angle of approximately ninety degrees, though the hinge allows for deviation from ninety degrees to conform with the type of seating being used by the user (e.g. car seat, chair, couch, etc.). According to some embodiments, the flexible part of the frame 102 provides a wide surface on which a user sits, their weight anchoring the bottom end 122 of the back portion 104 of the frame 102 so the support mechanism 108 reduces the pressure on the user's middle back. The flexibility of the frame 102 allows the seat portion 106 of the brace 100 to conform to the particular type of seating being used without causing discomfort.

The hinge point 118 between the two portions of the frame 102 allows the brace 100 to conform to different types of seats. It also permits a limited amount of relocation of a user, while wearing the brace 100. The sitting brace 100 is intended for use while sitting. One problem with conventional braces is over-bracing, or the use of a brace more than necessary. Walking is often the best activity to encourage healing of the back; however wearing a conventional brace while walking may inhibit or even reverse progress made. Nevertheless, compliance would be low for a brace 100 where a user is essentially locked into their seat. Advantageously, the sitting braces 100 contemplated herein may be worn while standing or walking, with the seat portion 106 hanging behind the user's thighs, according to various embodiments. Sitting and standing configurations of the brace 100, as well as hinges, will be discussed in greater detail in the context of FIGS. 3a and 3b, below.

As shown, the brace 100 comprises a support mechanism 108 that is coupled to the back portion 104 of the frame 102. In the context of the present description and the claims that follow, a support mechanism 108 is a mechanism that is able to expand and contract the back portion 104 of the frame 102, changing the distance between the top end 120 of the back portion 104 of the frame 102 and the hinge point 118. This expansion can exert force on the wearer's back, providing relief. The support mechanism 108 will be discussed in greater detail with respect to FIGS. 2a and 2b, below.

The brace 100 comprises at least a first pair 110 of shoulder straps. As shown, the first pair of shoulder straps 110 is coupled to the back portion 104 of the frame 102, looping under a user's arms so they may be lifted up, or hang from, the straps by the support mechanism 108, while sitting. In some embodiments, the first pair of shoulder straps 110 may be coupled to the back portion 104 above, or close to, the support mechanism 108, or more specifically, where the support mechanism 108 is coupled to the back portion 104 of the frame 102.

As previously discussed, the back portion 104 of the frame 102 is, at least in part, flexible. In some embodiments, the first pair 110 of shoulder straps may be part of this flexible portion of the frame 102. In one embodiment, the first pair of straps 110 may be integral with the back portion 104, while in another embodiment, the first pair 110 of straps may be coupled to the back portion 104. The first pair 110 of straps may be composed of a flexible material such as plastic, or any other material discussed above with respect to a flexible frame 102. In some embodiments, the first pair 110 of shoulder straps may be firm enough to maintain a shape, which may assist a user in putting the brace 100 on before sitting down.

The use of a flexible first pair 110 of straps in the braces 100 contemplated herein is advantageous over conventional braces, which tend to be either rigid, or (more commonly) non-existent. This flexibility makes the sitting brace 100 appropriate for use while driving, which requires a user to be able to turn their body far enough to check blind spots and safely operate a vehicle. Additionally, the flexibility increases the comfort, further increasing the likelihood of compliance with a treatment regimen. However, the flexibility is limited such that the first pair 110 of shoulder straps can also provide support that prevents the user's shoulders from coming forward. This promotes good sitting posture without limiting movement or even leading to a subsequent shoulder injury.

Some embodiments of the brace 100 may have a single pair of shoulder straps 110, from which the brace 100 hangs off the shoulder while the user is standing and by which the user receives support while sitting (i.e. the straps help hold the user up, relieving strain on their back). In other embodiments, including the non-limiting example shown in FIG. 1, the brace 100 may also comprise a second pair 112 of shoulder straps, allowing these two tasks to be split. According to various embodiments, the second pair 112 of shoulder straps is composed of a durable and soft material, providing longevity as well as comfort. As shown, in some embodiments, the second pair 112 of straps are coupled to the back portion 104 of the frame 102, above the support mechanism 108. As an option, the upper ends of the these straps 112 may overlap, and may be covered by an additional piece of material, strengthening the coupling and hiding the attachment point.

The first 110 and/or second 112 pairs of shoulder straps may be adjustable, such that they can be made to snuggly and comfortably fit the body of the user. In some embodiments, one or both pairs of shoulder straps 110,112 may be releasably coupled at the end distal to the back portion 104 of the frame 102, which may facilitate putting the brace 100 on. For example, as shown, in some embodiments the second pair 112 of shoulder straps may be attached to the abdominal strap 114 with hook-and-loop fasteners, allowing a user to adjust the fit of the brace 100 on their shoulders by changing the coupling point on the abdominal strap 114. As an option, one or both pairs of shoulder straps 110, 112 may be slightly elastic, providing a tighter fit. In other embodiments, both ends of one or both pairs of shoulder straps may remain attached to the brace 100, and the fit may be adjusted by changing the length of the straps, similar to the straps of a conventional backpack. In still other embodiments, the second pair of shoulder straps 112 may cross the user's body, anchoring near the hip opposite the shoulder. Such an arrangement of the straps may facilitate natural shoulder/opposite hip movement patterns. The use of the first and second pairs of shoulder straps 110, 112 is novel over conventional braces that rely on lifting at the abdomen. Lifting at three points instead of one makes the brace 100 more comfortable as well as more effective.

As shown, the brace 100 further comprises an abdominal strap 114 coupled to the back portion 104 of the frame 102. As the support mechanism 108 is used and the back portion 104 is lengthened, the upper body of the user is lifted upward by the shoulder straps 110 and the abdominal strap 114, reducing the pressure on their middle back. The abdominal strap 114 is coupled to the back portion 104 of the frame 102. In some embodiments the abdominal strap 114 may be directly coupled to a rigid portion of the frame 102 (e.g. coated metal tang).

In some embodiments, the abdominal strap 114 is coupled to the frame 102 fixedly (e.g. bolts, screws, pins, adhesive, incorporated into the coating of a rigid framework, integral with the frame 102 or a portion of the frame 102, etc.), while in others it may be releasably coupled (e.g. clips, toothed clamps, rotatable tabs, passing through an aperture in the frame 102, etc.) so it may be removed. A releasably coupled abdominal strap 114 may be advantageous, as it may be removed for cleaning, and/or replaced with a different sized strap more appropriate for a specific user.

As the support mechanism 108 extends the frame 102, the upper part of the user is lifted upward by the abdominal strap 114 and the shoulder straps 110. The abdominal strap 114 is adjustable, allowing a snug fit that can provide the needed lift. In some embodiments, including the non-limiting example shown in FIG. 1, the abdominal strap 114 may be releasably coupled at a variable size (e.g. using hook-and-loop fasteners, etc.) applied to opposite, overlapping ends of the strap 114. In other embodiments, other mechanisms known in the art may be used to close the strap 114 around the user and adjust its size, including but not limited to a smaller strap or straps with adjustable buckles or clips at either end, and the like.

According to various embodiments, the abdominal strap 114 may be composed of a soft, semi-elastic material that provides better grip on the user, and is comfortable. For example, in some embodiments, the abdominal strap 114 may comprise neoprene, other synthetic rubber materials, or similar materials. In some embodiments, the interior surface (e.g. the surface facing the user when the brace 100 is worn) may comprise a material chosen to provide a specific type of surface (e.g. able to slide over clothing without pulling, etc.).

The abdominal strap 114 is located above the lower coupling of the support mechanism 108, and comes under the rib cage of the user. Specifically, the abdominal strap 114 is positioned relative to the user, between the T8 and L2 vertebrae, according to various embodiments. Other embodiments may position the abdominal strap 114 elsewhere. The strap 114 is made sufficiently wide that it is comfortable while exerting a lifting force on the user. As a specific example, in one embodiment, the abdominal strap 114 may be 7 inches wide, with an overall length of 51.5 inches.

According to various embodiments, the sitting brace 100 may also comprise a lumbar cushion (not shown) on the inside (i.e. user-facing side) of the back portion 104 of the frame 102. In some embodiments, the lumbar cushion may be releasably coupled to the frame 102 such that it's position may be adjusted to meet the needs of a specific user. For example, in one embodiment, the lumbar cushion may be coupled to the frame 102 with hook-and-loop fasteners. In a specific embodiment, the lumbar cushion may be 2 inches thick, at its thickest. The lumbar cushion may be shaped to provide proper lumbar support, as is known in the art.

Figure 2A:
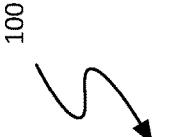
FIGS. 2A and 2B are front and back views, respectively, of the back brace of FIG. 1.
Figure 2A:
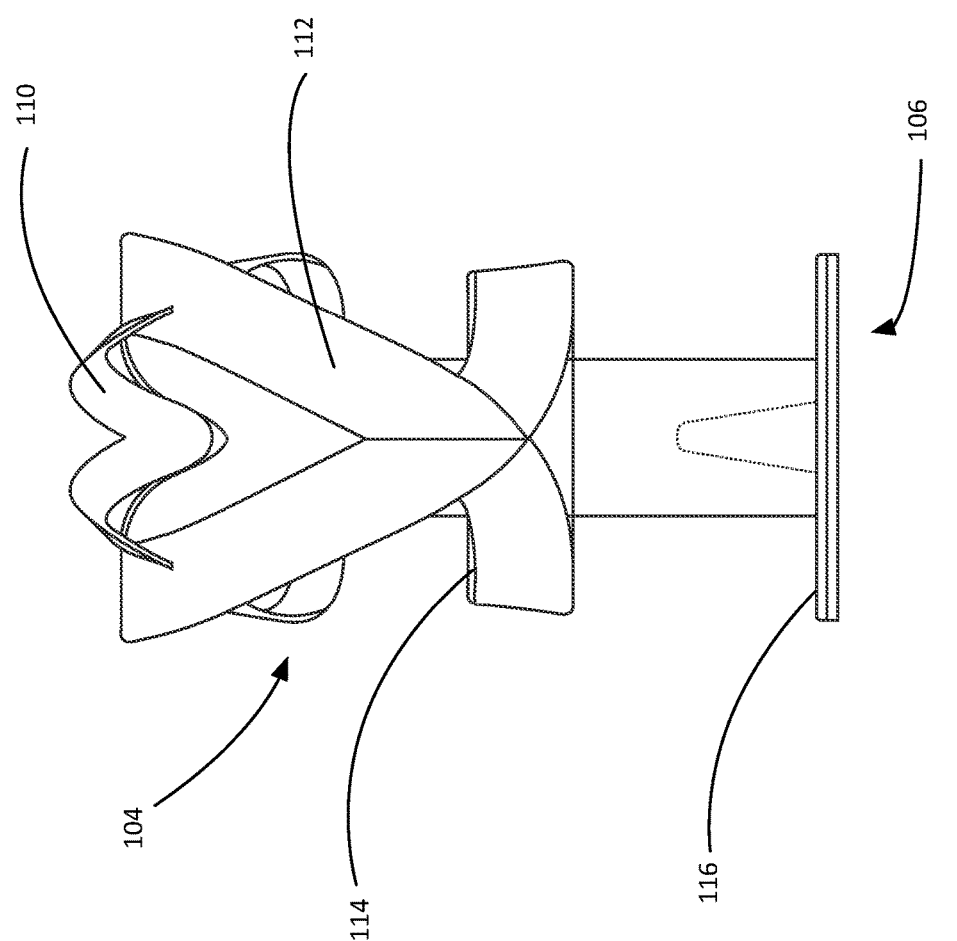
Figure 2B:
Figure 2B:
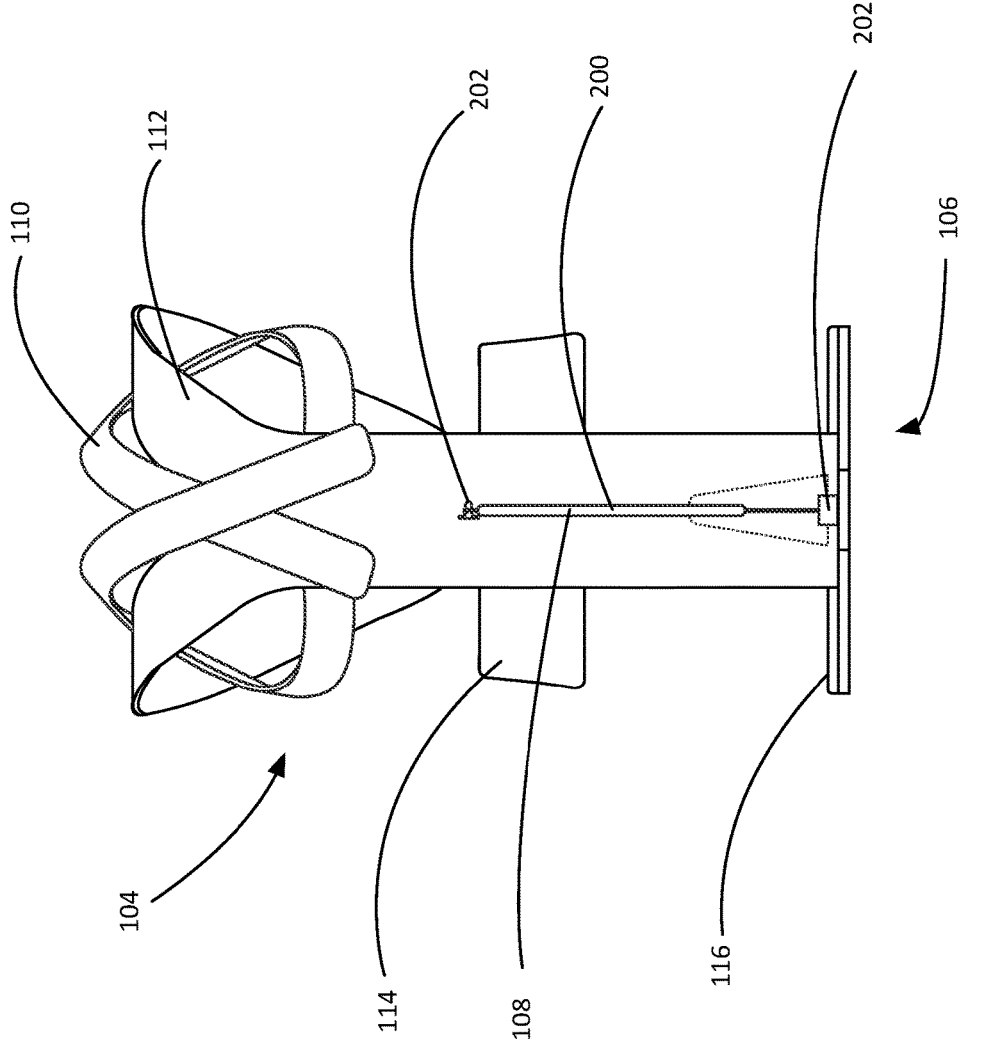
Figure 3A:
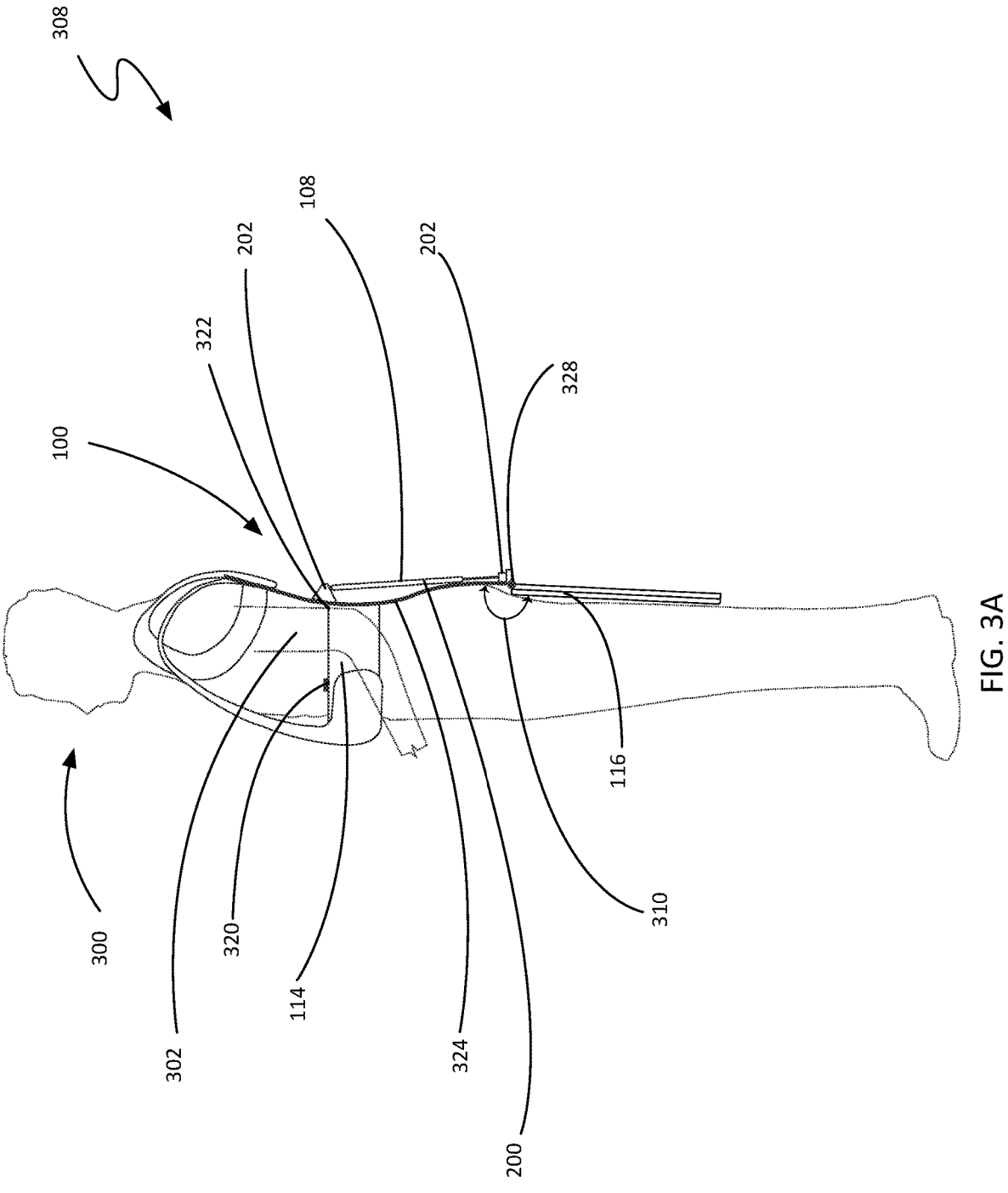
FIGS. 3A and 3B are side views of the back brace of FIG. 1 in standing and sitting configurations, respectively.
Figure 3B:
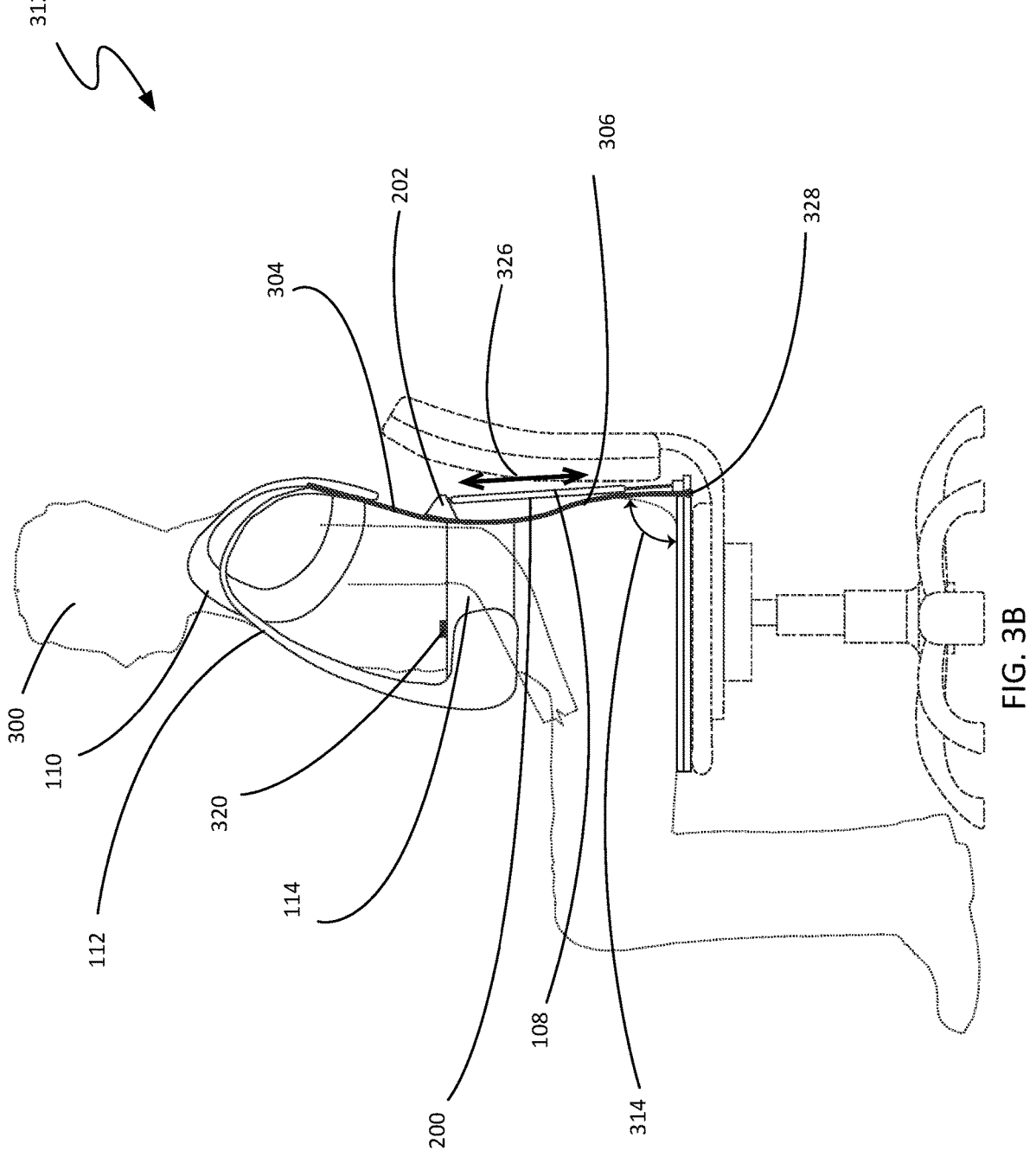

FIGS. 2A and 2B are front and back views, respectively, of the non-limiting example of a brace 100 shown in FIG. 1. FIGS. 3A and 3B are side views of the same non-limiting example in standing 308 and sitting 312 configurations, respectively. The shape of a wearer or user 300 is shown in FIGS. 3A and 3B to better illustrate the two configurations.

As previously discussed, the support mechanism 108 is a mechanism able to expand and contract, making it possible to exert an expanding force 326 on a user's back, providing relief. In some embodiments, the support mechanism 108 may be between the back portion 104 and the seat portion 106, moving the entire back portion away from the seat portion 106 when expanded. In other embodiments, the back portion 104 may be segmented, with the support mechanism 108 bridging the two segments, able to spread them apart to exert a force on the user's back. In still other embodiments, including the non-limiting examples shown in FIGS. 1-3, the support mechanism 108 may deform the back portion 104 of the frame 102, exerting a force (or maintaining a position after a force has been exerted) that elastically deforms the back portion 104. In other words, changing the distance between the top end 120 of the back portion 104 of the frame 102 and the hinge point 118. This extension allows the brace 100 to exert a force 326 on the users arms 302 with the shoulder straps 110 and on the torso with the abdominal strap 114, driving an upper portion 304 of the users 300 back away from a lower portion 306 of the users 300 back and relieving pressure on the middle back while sitting. According to various embodiments, the support mechanism 108 may be coupled directly to a rigid framework (e.g. coated metal tang), while in other embodiments it may be coupled directly to the back portion 104 in another manner. In other embodiments, the support mechanism 108 may be coupled to one part of the frame 102, and may be used to move another part of the brace 100, such as the shoulder and abdominal straps.

In some embodiments, the support mechanism 108 may be capable of extending the length of the back portion 104 between 0.5 inches and 1.5 inches. In other embodiments, the range of motion allowed by the support mechanism 108 may be more or less than this. As an option, in some embodiments, the support mechanism 108 may provide some form of visual indication of where it is currently set (e.g. an extension distance, a unitless setting, a color-coded scale, etc.). This may allow a user 300 to quickly return the support mechanism 108 to an ideal setting after going through the process of dialing it in when first starting to use the brace 100. This may be advantageous in embodiments where the support mechanism 108 must be adjusted before the user 300 puts on the brace 100.

In some embodiments, the user 300 may adjust the support mechanism 108 after putting on the brace 100, adjusting the size while sitting until it feels comfortable. Such embodiments have the advantage of being easy to setup and arrive at an ideal setting. Ease of use results in greater compliance. In other embodiments, the support mechanism 108 may need to be actuated before the brace 100 is put on, thereby avoiding the need to lift a portion of the wearer's body weight (e.g. lifting using the users legs, lifting using the support mechanism 108, etc.). This may be advantageous in terms of the weight and/or cost of the brace 100, since a less robust support mechanism 108 may be employed if it does not have to lift the user 300 up. Lifting support mechanisms will be discussed further with respect to FIG. 4, below.

According to various embodiments, the user 300 is able to control or modify the support mechanism 108, in one way or another. For example, in some embodiments, the user 300 is able to control when the support mechanism 108 is able to move, and when it is inhibited from expanding/contracting. For example, in one embodiment, the support mechanism 108 may simply be a series of lockable positions at which two portions of the frame 102 may be positioned, using any method known in the art (e.g. spring-loaded pins, locking bolts, etc.).

Other embodiments may provide a greater degree of granularity to the possible adjustments, and may further facilitate the adjustment of the support mechanism 108 while the brace 100 is being worn. For example, as shown in FIGS. 3A and 3B, some embodiments of the brace 100 may comprise a support mechanism control 320, which allows the user 300 to easily modify some aspect of the support mechanism 108 to adjust what it does to the user's back. Examples of support mechanism controls 320 include, but are not limited to, push buttons combined with a Bowden wire, knobs, cranks, levers, switches, and electronic controls including the use of a microcontroller.

As mentioned above, some embodiments may comprise a support mechanism 108 that is able to be toggled between a locked state 318 where the support mechanism 108 is in some way inhibited in movement, and an unlocked state 316 where the support mechanism 108 is able to expand and contract. In some embodiments, the locked state may be rigid, with the support mechanism 108 being held firmly in place without much or any deviation. In other embodiments, the locked state may more accurately be described as a dampened state, where motion is still possible, but strongly dampened. The use of a dampened locked state is advantageous, as it may be configured to be sufficiently firm as to exert the force needed to provide relief, yet dampened enough to gently adjust with small movements of the user, such as adjusting their position in a seat. Such small movements may be uncomfortable in a rigidly held brace; a brace 100 making use of a dampened locked state may provide greater comfort and thus greater compliance, without sacrificing efficacy.

The non-limiting example of a brace 100 shown in FIGS. 1-3 makes use of a support mechanism 108 having a dampened locked state. As shown, the support mechanism 108 is a dampened lockable gas spring (hereinafter referred to as a gas spring 200). According to some embodiments, this gas spring 200 is able to remain flexible in both directions while a valve is held open (e.g. a valve actuated by a Bowden wire coupled to a push button, etc.). When the valve is closed, the gas spring 200 may still be able to move the entire length of the stroke, but with increasing resistance. Such a support mechanism 108 may be configured to be so dampened that shocks may be absorbed comfortably (e.g. scooting over on a bench while wearing the brace 100, etc.), yet still provide support and relief while the user is sitting more or less stationary. Such a support mechanism 108 may also be more comfortable for use while in a car. The rigid frames of conventional braces translate all the bumps of the road to the user, while the brace 100 contemplated herein may dampen the bumpiness while supporting the user and providing relief. Other examples of support mechanisms 108 having dampened locked states include, but are not limited to, coiled springs (e.g. twisting the spring to increase dampening once proper length found, etc.), hydraulic springs, and any other adjustable dampened springs known in the art.

In some embodiments, the support mechanism 108 may be lockable in both directions. In other words, when placed in a locked state, both expansion and contraction are inhibited, dampened, or rigidly prevented. As a specific example, the gas spring 200 shown in FIGS. 1-3. In other embodiments, the support mechanism 108 may be lockable (e.g. inhibited, dampened, prohibited) in a single direction. For example, in some embodiments, the support mechanism 108, when in a locked state, may be able to expand, but not contract. In some embodiments, the contraction may be prevented beyond a set point, independent of the expansions that occur while in the locked state. In other embodiments, the movement of the support mechanism 108 may be one way, such that each expansion establishes a new point at which contraction is inhibited/dampened/forbidden.

As a specific example, in one embodiment, the support mechanism 108 may comprise a ratcheting gear engaged with a plurality of teeth running parallel to the back portion 104. The rotation of a wheel may turn a ratcheting gear engaged with the teeth, climbing upward as the wheel is turned but unable to go back down unless a locking mechanism of the ratchet is opened, as is known in the art. In some embodiments, the upward movement may be executed by the user simply rising up (e.g. sitting up straighter, pushing up from the seat, etc.). As the user rises, the gear turns and moves along the teeth, with backward movement prevented by the ratchet.

In some embodiments, the user 300 is able to modify the support mechanism 108 to favor a particular location by actuating a support mechanism control 320 when the support mechanism 108 is in the desired position. In other embodiments, the user 300 may adjust the support mechanism 108 in ways that do not require the desired position to be achieved before locking. For example, in some embodiments, the user 300 may be able to modify the support mechanism 108 such that it behaves differently, but along the same range of motion (e.g. adjusting the expanding force 326 exerted by the support mechanism 108, which is biased to expand.

As stated above, the support mechanism 108 is coupled to the back portion 104 of the frame 102, according to various embodiments. The support mechanism 108 may be coupled to the frame 102 in a number of ways. In some embodiments, the couplings used with the support mechanism 108 may permit the user 300 to move to some degree while wearing the brace 100 and seated. For example, in some embodiments, the support mechanism 108 may be coupled to the frame 102 using one or more pivot couplings 202 (e.g. ball pin brackets, u brackets, etc.), that permit one or more degrees of freedom. As a specific example, FIGS. 2 and 3 show the use of an upper pivot coupling 202 permitting pivoting in (or roughly parallel to) the sagittal plane (i.e. the plane bisecting the body along the spine with legs and arms intact), and a lower pivot coupling 202 permitting pivoting in (or roughly parallel to) the coronal or frontal plane (i.e. the plane bisecting both arms and both legs). Such a configuration would allow a user to twist without compromising the support provided, a motion of great utility when driving. In some embodiments, the support mechanism 108 may be coupled entirely to the back portion 104. In other embodiments, one end of the support mechanism 108 may be coupled to the back portion 104, and the other end may be coupled to the hinge point 112, or the seat portion 106.

FIGS. 3a and 3b show a non-limiting example of the brace 100 in a standing configuration 308 and a sitting configuration 312, respectively. As previously discussed, the braces 100 contemplated herein are able to be worn while standing/walking, without interfering with such activity like a conventional brace. The brace 100, or more specifically the frame 102, is movable between a standing configuration 308 and a sitting configuration 312 as the user 300 transitions from standing to sitting on the seat cushion 116. In the standing configuration 308, there is a first angle 310 between the seat portion 106 and the back portion 104. In the sitting configuration 312 there is a second angle 314 between the seat portion 106 and the back portion 104. That second angle 314 is smaller than the first angle 310. When in the sitting configuration 312, the support mechanism 108 is reducing the force exerted on the user's back by supporting the user 300 with the back portion 104 of the frame 102 through the shoulder straps 110 and abdominal strap 114, and driving an upper portion 304 of the user's back away from a lower portion 306 of the user's back to provide relief. According to various embodiments, the abdominal strap 114 is positioned on the back portion 104 of the frame 102 between the T8 322 and L2 324 vertebrae of the user 300.

In some embodiments, while in the standing configuration 308 the seat portion 106 may dangle behind the users thighs, swinging freely. In other embodiments, the back portion 104 and seat portion 106 may be hingedly coupled through a biased hinge 320 that is biased to drive the frame 102 toward the sitting configuration 312 (i.e. toward a second angle 314 that is smaller than the first angle 310). This facilitates the transition from standing to sitting for a user wearing the brace 100, as the biased hinge swings the seat under them as they lower. In some embodiments, the seat portion 106 may be able to swing all the way to a second angle of essentially zero, with the seat folded up against the back portion 104. This may facilitate storage and/or transport when not in use.

As a specific use example, a user 300 may first put on the brace 100 by placing their arms 302 through the shoulder straps 110, 112, holding the brace 100 in place while they close the abdominal strap 114 around their body. Once the abdominal strap 114 is coupled snug against the user 300, the shoulder straps 110,112 may be adjusted and/or closed to fit snug against the user 300. The user 300 then sits down, with the seat portion 106 being biased against their thighs so it does not get caught while sitting down. In some embodiments, the support mechanism 108 may be adjusted after the user is sitting, allowing the user to extend the back portion 104 of the frame 102 until they feel pressure relieved from their back. In other embodiments, the user may perform such an adjustment before sitting down, or even before putting the brace 100 on.

Figure 4:
FIG. 4 is a perspective view of another back brace for sitting.
Figure 4:
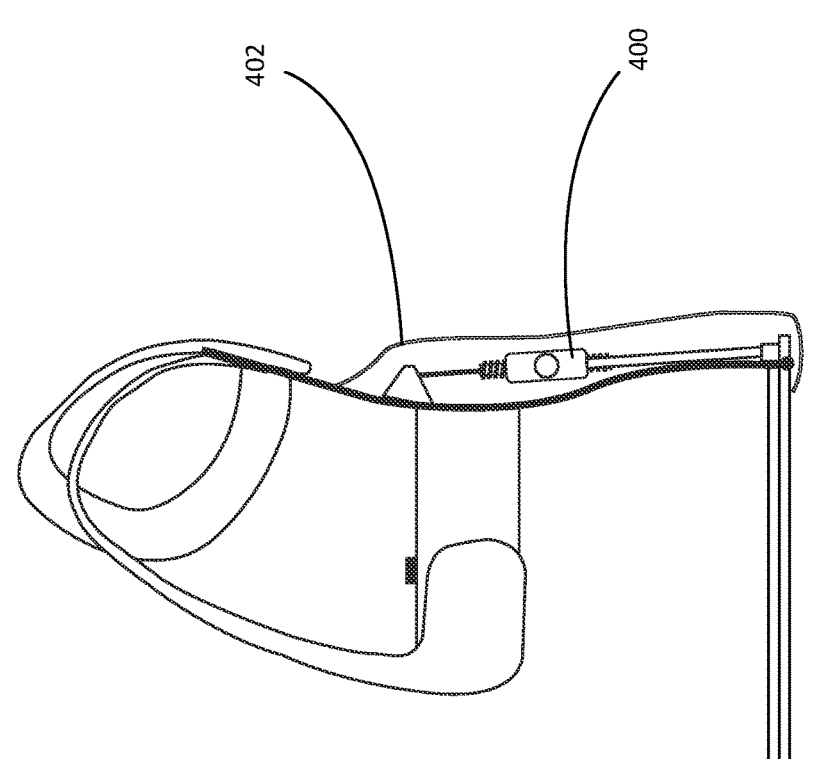

FIG. 4 is a perspective view of another non-limiting example of a back brace 100 for sitting. Specifically, FIG. 4 shows an embodiment of the brace 100 making use of a lifting jack 400 as the support mechanism 108. In some cases, it may be difficult for a user to raise themselves up high enough under their own power, and maintain that position long enough to lock the support mechanism 108, as is necessary in some, but not all embodiments. Other embodiments may have a support mechanism 108 that goes beyond maintaining an expanded state, but to actually lift the user's upper body upward until the desired force is being exerted on their back and providing relief.

In the context of the present description and the claims that follow, a lifting jack 400 is any linear lifting device capable of, at least in part, elevating a portion of a user's bodyweight to a therapeutic level. Examples include, but are not limited to, scissor jacks, hydraulic jacks, screw jacks, rack and pinion, ratcheting gear drives, linear actuators, and the like. While such support mechanisms 108 may tend to be bulkier and more expensive than other support mechanisms 108, they may provide embodiments of the brace 100 easier for weaker wearers to use.

Some embodiments may also comprise a covering 402 to shield the support mechanism 108 and to protect seating when the user 300 is seated. In some embodiments, the covering 402 may be composed of a fabric, like a heavy nylon material (e.g. backpack material, etc.), or the like. In other embodiments, the covering may be non-fabric, such as thermoplastic or other material.

Where the above examples, embodiments and implementations reference examples, it should be understood by those of ordinary skill in the art that other examples of a back brace for sitting could be intermixed or substituted with those provided. In places where the description above refers to particular embodiments of back braces for sitting, it should be readily apparent that a number of modifications may be made without departing from the spirit thereof and that these embodiments and implementations may be applied to other back braces as well. Accordingly, the disclosed subject matter is intended to embrace all such alterations, modifications and variations that fall within the spirit and scope of the disclosure and the knowledge of one of ordinary skill in the art.

What is claimed is:

1. A therapeutic back brace for sitting, comprising: a frame having a back portion, a seat hingedly coupled to the back portion through a biased hinge biased to a seated position from an extended position, the back portion being flexible, and a vertical extender comprising a gas spring, the vertical extender being a support mechanism connected to the back portion of the frame at a first location and coupled to the seat at a second location, the vertical extender positioned between the back portion and the seat; a first pair of shoulder straps releasably coupled to the back portion of the frame and configured to extend over a user's respective left and right shoulders and attach to the back portion after extending beneath the user's respective left and right shoulders; an abdominal strap releasably coupled to the back portion of the frame and having respective distal ends configured to extend around a user's midsection at a position between the user's T8 and L2 vertebrae, the respective distal ends configured to releasably couple to each other using hook and loop fasteners; a second pair of shoulder straps releasably coupled to the back portion of the frame and having respective distal ends configured to extend over the user's respective left and right shoulders, cross in front of the user and attach to the abdominal strap using hook and loop fasteners on respective right and left sides of the user's midsection; wherein the first location at which the vertical extender is coupled to the back portion is located between the abdominal strap and the first pair of shoulder straps, and the vertical extender is configured to lengthen to move the back portion away from the seat and to lift the upper body of the user through the shoulder straps and the abdominal strap; and a lumbar cushion releasably coupled to the frame with hook and loop fasteners and configured to be positioned between the frame and the user at a position between the user's T8 and L2 vertebrae; wherein the therapeutic back brace has a standing configuration and a sitting configuration, the standing configuration comprising a first angle between the seat and the back portion, the sitting configuration comprising a second angle between the seat and the back portion smaller than the first angle, and wherein the vertical extender is configured to reduce the force exerted on the user's back by supporting the user with the back portion of the frame and driving an upper portion of the user's back away from a lower portion of the user's back when the user is strapped into the therapeutic back brace.

2. The therapeutic back brace of claim 1, wherein the vertical extender is biased to exert an expanding force on the back portion of the frame, driving the top end of the back portion away from the hinge point, the expanding force adjustable by the user.

3. The therapeutic back brace of claim 1, wherein the support mechanism is movable by the user between an unlocked state that allows the support mechanism to lengthen and shorten, and a locked state that restricts the support mechanism from shortening.

4. The therapeutic back brace of claim 1, wherein the support mechanism is movable by the user between an unlocked state that allows the support mechanism to lengthen and shorten, and a locked state that restricts the support mechanism from lengthening and shortening.

5. A therapeutic back brace for sitting, comprising: a frame having a back portion, a seat hingedly coupled to the back portion, and a vertical extender being a support mechanism connected to the back portion of the frame at a first location and coupled to the seat at a second location, the vertical extender positioned between the back portion and the seat; a first pair of shoulder straps releasably coupled to the back portion of the frame and configured to extend over a user's respective left and right shoulders and attach to the back portion after extending beneath the user's respective left and right shoulders; an abdominal strap releasably coupled to the back portion of the frame and having respective distal ends configured to extend around a user's midsection at a position between the user's T8 and L2 vertebrae; a second pair of shoulder straps releasably coupled to the back portion of the frame and having respective distal ends configured to extend over the user's respective left and right shoulders, cross in front of the user, and attach to the abdominal strap on respective right and left sides of the user's midsection; wherein the first location at which the vertical extender is coupled to the back portion is positioned between the abdominal strap and the first pair of shoulder straps, and the vertical extender is configured to lengthen to move the back portion away from the seat and to lift the upper body of the user through the shoulder straps and the abdominal strap; a lumbar cushion releasably coupled to the frame with hook and loop fasteners and configured to be positioned between the frame and the user; and wherein the vertical extender is configured to reduce the force exerted on the user's back by supporting the user with the back portion of the frame and driving an upper portion of the user's back away from a lower portion of the user's back when the user is strapped into the therapeutic back brace.

6. The therapeutic back brace of claim 5, wherein the vertical extender is biased to exert an expanding force on the back portion of the frame, driving the top end of the back portion away from the hinge point, the expanding force adjustable by the user.

7. The therapeutic back brace of claim 5, wherein the support mechanism is movable by the user between an unlocked state that allows the support mechanism to lengthen and shorten, and a locked state that restricts the support mechanism from shortening.

8. The therapeutic back brace of claim 5, wherein the support mechanism is a gas spring.

9. The therapeutic back brace of claim 5, wherein the support mechanism is a lifting jack.

10. A therapeutic back brace for sitting, comprising: a frame having a back portion, a seat coupled to the back portion and a vertical extender being a support mechanism coupled to the back portion of the frame at a first location and coupled to the seat at a second location, the vertical extender positioned between the back portion and the seat; a first pair of shoulder straps coupled to the back portion of the frame and configured to extend over a user's respective left and right shoulders and attach to the back portion after extending beneath the user's respective left and right shoulders; an abdominal strap coupled to the back portion of the frame and having respective distal ends configured to extend around a user's midsection; wherein the first location at which the vertical extender is coupled to the back portion is positioned between the abdominal strap and the first pair of shoulder straps, and the vertical extender is configured to lengthen to move the back portion away from the seat and to lift the upper body of the user through the shoulder straps and the abdominal strap; and wherein the vertical extender is configured to reduce the force exerted on the user's back by supporting the user with the back portion of the frame and driving an upper portion of the user's back away from a lower portion of the user's back when the user is strapped into the therapeutic back brace.

11. The therapeutic back brace of claim 10, wherein the back portion of the frame is hingedly coupled to the seat.

12. The therapeutic back brace of claim 10, further comprising a second pair of shoulder straps releasably coupled to the back portion of the frame and having respective distal ends configured to extend over the user's respective left and right shoulders, cross in front of the user, and attach to the abdominal strap on respective right and left sides of the user's midsection.

13. The therapeutic back brace of claim 10, wherein the abdominal strap is further configured to extend around a user's midsection to at a position between the user's T8 and L2 vertebrae.

14. The therapeutic back brace of claim 10, wherein the vertical extender is biased to exert an expanding force on the back portion of the frame, driving the top end of the back portion away from the hinge point, the expanding force adjustable by the user.

15. The therapeutic back brace of claim 10, wherein the support mechanism is movable by the user between an unlocked state that allows the support mechanism to lengthen and shorten, and a locked state that restricts the support mechanism from shortening.

16. The therapeutic back brace of claim 10, wherein the support mechanism is movable by the user between an unlocked state that allows the support mechanism to lengthen and shorten, and a locked state that restricts the support mechanism from lengthening and shortening.

17. The therapeutic back brace of claim 10, wherein the support mechanism is a gas spring.

18. The therapeutic back brace of claim 10, wherein the support mechanism is a lifting jack.

19. The therapeutic back brace of claim 10, a lumbar cushion releasably coupled to the frame with hook and loop fasteners and configured to be positioned between the frame and the user.

20. The therapeutic back brace of claim 10, wherein at least one of the first pair of shoulder straps and the abdominal strap is further configured to be releasably coupled to the back portion of the frame.

* * * * *